US005798267A

United States Patent [19]

Harasymiw

[11] Patent Number: 5,798,267

[45] Date of Patent: Aug. 25, 1998

[54] METHOD FOR DETERMINING ALCOHOL CONSUMPTION RATES

[76] Inventor: James W. Harasymiw, W243 S7630 Evergreen Dr., Mukwonago, Wis. 53140

[21] Appl. No.: 481,656

[22] Filed: Jun. 7, 1995

Related U.S. Application Data

[63] Continuation-in-part of Ser. No. 275,101, Jul. 14, 1994, abandoned.

[51] Int. Cl.[6] .......... G01N 33/48; G01N 33/72

[52] U.S. Cl. .......... 436/97; 436/67; 436/71; 436/66; 436/79; 436/80; 436/81; 436/86; 436/88; 436/95; 436/96; 436/97; 436/98; 436/99; 436/108; 436/132

[58] Field of Search .......... 436/67, 71, 66, 436/79, 80, 81, 86, 88, 95, 132, 108, 96–99

[56] References Cited

U.S. PATENT DOCUMENTS

| | | | |
|---|---|---|---|
| 4,463,098 | 7/1984 | Hoberman | 436/67 |
| 4,626,355 | 12/1986 | Joustra et al. | 210/635 |
| 4,770,996 | 9/1988 | Tabakoff | 435/18 |
| 4,814,280 | 3/1989 | Peterson | 436/128 |
| 5,066,583 | 11/1991 | Mueller | 435/18 |
| 5,081,011 | 1/1992 | Bradley | 435/7.24 |
| 5,126,271 | 6/1992 | Harasymiw | 436/71 |

OTHER PUBLICATIONS

N. Blanckaert et al. *J. Lab. Clin. Med.* 1980, 96, 198–212.
M. Chan–Yeung et al. *Am. J. Clin Pathol.* 1981, 75, 320–326.
C. DiPadova et al. *Digestion* 1982, 24, 112–117.
R.S Ryback et al. *Substance Alcohol Act. Misuse* 1983, 4, 217–224.
D. Stamm et al. *J. Clin. Chem. Clin.Biochem.* 1984, 22, 65–77.
J.R. Evans et al. *Ann. Clin. Biochem.* 1984, 21, 261–267.
B. Dworkin et al. *Digest. Diseas. Sci.* 1985, 30, 838–844.
A.K. Rawat et al. *Alcohol* 1986, 3, 139–143.
A. Sieg et al. *Gastroenterology* 1987, 93, 261–266.
A. Ahlgren et al. *Scand. J. Clin. Lab. Invest.* 1988, 48, 319–326.
G. Börsch et al. *J. Clin. Chem. Clin. Biochem.* 1988, 26, 509–519.
Y. Takahashi et al. *Hepatology* 1994, 19, 1065–1071.
G. Fex et al. *Ann. Clin. Biochem.* 1982, 19, 345–349.
A.G. Shaper et al. *Ann. Clin. Biochem.* 1985, 22, 50–61.
P.Wallace et al. *British Medical J.* 1985, 290, 1949–1953.
V.N. Hillers et al. *Alcohol Alcohol.* 1985, 21, 199–205.
M.J. Eckart et al. *Prog. Neuro–Psychopharm. Biol. Psyc.* 1986, 10, 135–144.
C.M. Schnitzler et al. *Alcohol Alcohol.* 1988, 23, 127–132.
M.J. Lichtenstein et al. *Alcohol. Clin. Exp. Res.* 1989, 13, 626–630.
M. Nystrom et al. *Alcohol. Clin. Exp. Res.* 1992, 16, 93–97.
P. Sillanaukee *Arch. Pathol. Lab. Med.* 1992, 116, 924–929.
P. Sillanaukee et al. *Europ. J. Clin. Invest.* 1993, 23, 486–491.

*Primary Examiner*—Arlen Soderquist
*Attorney, Agent, or Firm*—Reinhart, Boerner, Van Deuren, Norris & Rieselbach, s.c.

[57] ABSTRACT

A method for assessing or determining alcohol consumption rates including using a blood specimen from a human subject to develop an individual blood constituent panel; comparing the individual panel with a reference blood constituent panel to provide categories corresponding to rates of alcohol consumption; and identifying the category of consumption rate. The methods of the invention can be varied through modification of one of several statistical models used therewith to preferentially weigh the analysis and identify one consumption category over another. Multivariate and similar such statistical techniques correlate comparisons of individual/subject blood and reference panel constituents with recognized consumptions rates.

31 Claims, 1 Drawing Sheet

Ph (Probability of Heavy Drinking)
0.9
0.8
0.7
0.6
0.5
0.4
0.3
0.2
0.1
0
Overlap = .02
Sens. = .95
Spec. = .95
142 subjects
P h > .95
Critical Value for Sensitivity and Specificity
36 subjects
P h < .05
Light Drinkers
(n = 42)
Heavy Drinkers
(n = 161)

METHOD FOR DETERMINING ALCOHOL CONSUMPTION RATES

This application is a continuation-in-part of U.S. application Ser. No. 08/275,101, filed Jul. 14, 1994, now abandoned.

BACKGROUND OF THE INVENTION

This invention is related generally to methods for evaluating individuals in terms of their rates of alcohol consumption and, more particularly, a method for identifying and/or screening those individuals of a larger population whose consumption rates indicate problematic behavior and/or alcoholic tendencies.

Alcoholism is a serious human health issue and it has been predicted that it will affect about 16% of the population. Mortality rates among alcoholics are two to three times the rate for the general population and it has been suggested that it is one of the leading preventable causes of death, injury, illness and impaired functioning. In 1994, the National Institute on Alcoholism and Alcohol Abuse cited reports estimating the total societal costs for alcoholism in 1993 of about $140 billion dollars. Considerable effort has been directed toward the development of techniques for diagnosing alcoholism or excessive consumption rates. One technique involves the examination of blood serum variables, while the remaining three are psychological assessments.

An example of earlier work based on examination of blood serum variables is described in a paper titled "Biochemical and Hematological Correlates of Alcoholism" by Ryback et al., published in *Research Communications in Chemical Pathology and Pharmacology*, Vol. 27, No. 3, March 1980. The authors considered a number of blood serum constituents in several combinations. Best accuracy (86% in the combined alcoholic group) resulted when they used the SMA 12 (12 standard constituents), SMA 6 (6 standard constituents) and Hematological (7 standard constituents) tests in combination. Table 2 of the paper shows the 25 total constituents. The authors experienced 16% false negatives, i.e., 16% of the alcoholics were identified as being nonalcoholics. No false positives were experienced.

Two aspects of the Ryback et al. paper are particularly important. One is that the prior probabilities (a reflection of apparent historical fact) used by the authors were 0.5 for medical controls, 0.4 for treatment program alcoholics and 0.1 for alcoholics admitted to medical wards. These values were selected arbitrarily but were influenced by a study which indicated that about 50% of a group of patients admitted to a Veterans Hospital had alcohol related problems.

The authors further indicate that adjustment of the prior probabilities by +or −0.1 resulted in no significant change in the accuracy of the discrimination between alcoholics and nonalcoholics. They also stated that "[t]he prior probabilities could be changed from 0.4 to 0.8 in the medical controls and from 0.6 to 0.2 in the alcoholics with no significant change in the accuracy of discrimination. " The other particularly important aspect of the Ryback et al. paper is a quotation appearing on page 545. There, the authors state that "[s]ignificant relationships involving drinking variables were observed for all tests except cholesterol . . . " (emphasis added).

Another relevant paper dealing with examination of blood serum variables is titled "Hematological Concomitants of Alcoholism: Development and Validation of a Clinical Screening Technique" by Hawkins et al., published in *Journal of Substance Abuse Treatment*, Vol. 1, 1984. While the age and sex of the subjects were noted, no observation was made as to whether such factors are of use in identifying abuse. Hawkins et al. used two different multi-variate discriminant analyses which yielded classification accuracies significantly different from one another. The quadratic analysis correctly classified about 94% of alcoholics while the stepwise analysis correctly classified about 79% of alcoholics. The authors' caveat states " . . . This technique is unlikely to provide sufficiently precise classification for anything other than medical screening purposes, which should then be bolstered with independent substantiation before arriving at a diagnosis."

Some of the earlier work involving analysis of blood serum variables considers the blood chemistry constituents selenium and magnesium. Such work is described in a paper titled "Diminished Blood Selenium Levels in Alcoholics" by Dworkin et al. published in *Alcoholism: Clinical and Experimental Research*, Vol. 8, No. 6, November/December 1984. The authors have noted that alcoholics have a reduced level of selenium. As stated in the Abstract, this fact is of concern to the authors "[s]ince selenium deficiency can produce a spectrum of organ injury . . . the relationship of selenium deficiency to alcohol-induced organ injury deserves further study."

Clearly, the subjects had already been identified as alcohol abusers—the focus of the research was prospective organ damage. And the authors observe that low selenium levels can also result from diet, cancer, severe burns and kwashiorkor. In other words, a low selenium blood serum level per se was not appreciated as having value in the diagnosis of alcohol abuse. A similar paper is "Decreased Serum Selenium in Alcoholics as Related to Liver Structure and Function" by Korpela et al. published in *The American Journal of Clinical Nutrition*, July. 1985.

Other work involving blood serum variables is described in a paper titled "Serum Zinc, Copper, and Ceruloplasmin Levels in Male Alcoholics" by Wu et al. published in *Biological Psychiatry*, Vol. 19, No. 9, 1984. The authors used blood samples from known alcoholics having an average daily consumption level of about 294 mL of absolute alcohol. They noted the reciprocal relationship between serum zinc and copper levels and found that the serum zinc level in alcoholic patients was lower than that of a control group. While the serum copper level was higher, the authors indicate it was a not statistically significant. The authors also observe that earlier workers have found a psychiatric condition, i.e., depression, to be associated with lower serum zinc levels and low zinc, copper and ceruloplasmin levels. In an added note, the authors also state, with respect to serum levels of calcium and magnesium, that "[t]heir differences were not statistically significant between alcoholics and controls."

Yet another paper dealing with blood serum variables is titled "Alcohol Consumption and High Density Lipoprotein Cholesterol Concentration Among Alcoholics" by Dai et al. published in *American Journal of Epidemiology*, Vol. 122, No. 4, 1985, wherein findings are presented indicating a largely inconclusive relationship of HDL cholesterol levels and consumption rates: HDL cholesterol increased with increasing alcohol consumption up to about 450 mL of ethanol consumption per day, then decreased or appeared to decrease. The authors primarily examined the relationship between alcohol consumption and the level of HDL subclasses HDL2 and HDL3.

Currently, most persons suspected of having a drinking problem are screened using psychological tests, some of which are mentioned below. A drawback to reliance on such tests to the exclusion of other considerations is that their results depend heavily upon the subject's good will, i.e., information as voluntarily disclosed by the subject, as well as other subjective criteria such as personality, demeanor, appearance, and the like. Because denial is a common trait among alcoholics, various manifestations of the denial syndrome can skew the test results to the detriment of an accurate assessment/diagnosis.

One widely-used psychological approach, empirical in nature, is known as the McAndrew scale of the Minnesota Multiphasic Personality Inventory (MMPI). The McAndrew scale is representative of other similar approaches and generally accepted as a reliable method of alcohol assessment. It has been demonstrated to correctly classify about 84% of alcoholics when a cutoff score of 24 raw points is used. There are about 10 false negatives and 14 false positives using such cutoff point.

In general, the McAndrew test is composed of those items from the MMPI to which alcoholics respond differently than does the general population. The subject is required to respond to "true" or "false" questions which include latent "check" questions to detect whether the subject has answered consistently. It should be noted, however, that the accuracy of the McAndrew scale has come into question because it also seems to respond to other non-alcohol forms of drug addiction, as well as to general deviancy.

Irrespective of the approach or method used, it should be appreciated that when tests are used for certain purposes, e.g., screening job applicants, false positives present a certain risk for the tester. The subject/applicant may be denied employment, promotion, or personal advancement if s/he is falsely identified as a heavy drinker or alcoholic. Ryback et al. euphemistically refers to this happenstance as "clinically embarrassing." In more practical terms, it can give rise to actual and/or legal liability.

Another psychological approach involves the use of consumption pattern questionnaires. The Khavari Alcohol Test is an example of such an approach. In studies of validity and reliability, the Khavari test has consistently and relatively accurately differentiated between alcoholic and control groups. The Khavari test considers the drinking patterns of individuals (as provided by such individuals) and compares such patterns with established statistical drinking norms. These comparisons are then used for making diagnostic decisions.

Yet another psychological approach involves a variety of questionnaires which attempt to count incidents of problems or behaviors thought to be symptomatic of alcoholism. The Michigan Alcoholism Screening Test (MAST), and the National Council on Alcoholism Criteria for the Diagnosis of Alcoholism (CRIT) are examples. In a modified form known as MODCRIT, the latter is used clinically.

U.S. Pat. Nos. 3,954,409 (Hsia), 3,645,688 (Smernoff), 4,115,062 (Morre et al.), 4,820,628 (Weitz), 4,753,890 (Smith-Lewis et al.), 4,820,647 (Gibbons) and 4,837,164 (Glick) describe methods of analyzing blood serum constituents. Such patents do not suggest how such methods might be used for determining the consumption rate of alcohol or for diagnosing alcoholism.

The Smernoff and Hsia patents involve cholesterol in blood and describe methods for recognizing the type and presence of hyperlipoproteinemia (Smernoff) or for assessing the risk of coronary heart disease (Hsia). The Smith-Lewis et al. patent describes a method for determining magnesium ions in, among other things, blood serum and plasma. While the patent says the determination of such ion can be used for diagnosing and treating various ailments, alcohol consumption/abuse is neither mentioned nor suggested.

On the other hand, there are situations where a false positive causes little or no adversity to anyone but the risk of a false negative is relatively great. For example, alcoholism in persons under consideration for alcoholism treatment should be identified with a relatively high level of certainty. Another example involves selection of persons for highly sensitive tasks requiring, e.g., certain unusual physical skills or a high level of confidentiality. The public interest in selection accuracy may be sufficiently high so as to outweigh considerations of adversity arising from a false positive. In those instances, the sole question is not how much the subject is drinking but whether s/he is drinking alcoholically. Identification of such individuals is enhanced by using only two prior rather than three probability values: 0.5 and 0.5 rather than the more typical 0.9 and 0.1 Ryback values.

The prior art may be summarized by observing that it fails to appreciate how the actual level or rate (within somewhat broad ranges) at which an individual is consuming alcohol can be relatively quickly determined by analyzing the serum variables in a blood sample taken from such individual. A method for making such a determination while minimizing false positive results would be an important advance in identifying individuals having problematic consumption rates and, in the extreme cases, diagnosing alcoholism. This is especially true if the level of accuracy is sufficient to permit the method to be the sole or at least predominant, clinical diagnostic tool.

OBJECTS OF THE INVENTION

It is an object of this invention to provide an improved method for determining the rate of consumption of alcohol which overcomes the problems, limitations and shortcomings of the prior art.

Another object of this invention is to provide a non-subjective method for determining the rate of consumption of alcohol such that any evaluation or assessment is objective.

Yet another object of this invention is to provide an improved method for identifying categories of alcohol consumption which can serve as a singular, or at least predominant, tool in diagnosing problematic alcohol-related behavior.

Another object of this invention is to provide an improved method for determining rates of alcohol consumption rate which is efficient, economical and easily used in combination with standard blood work.

Another object of this invention is to provide a method for identifying categories of alcohol consumption which can be used with equal effect in conjunction with, and without limitation, pre-employment screening, post-accident assessment, chemical drug trials to, inter alia indicate alternative treatment approaches or concurrent drug abuse and pre-prescription diagnosis of potential drug interaction.

Another object of this invention is provide a method for identifying and/or assessing alcohol consumption levels with or without correlation to daily ingestion volumes, notwithstanding periods of abstinence.

Another object of this invention is to provide a method which can be used in conjunction with standard and/or widely-used alcohol markers, such that they are used selectively and more effectively as part of a reflex test to confirm a given consumption category and/or minimize false positive results.

Another object of the present invention is to provide a method for identifying alcohol consumption categories which utilize a previously-compiled base of blood panels and/or blood work up results, notwithstanding the circumstances under which the blood samples, panels, and/or results were obtained.

Another object of the invention is to provide a method for use in conjunction with one of several statistical techniques which permits manipulation of standard reference panels and individual/subject panels to determine a minimum number of panel constituents or combination of a minimal number of constituents and/or other factors which can be utilized to meet accuracy, sensitivity, and other-related performance criteria, with or without subsequent reflex testing.

Another object of this invention is to provide a method for use in conjunction with one of several statistical techniques to predict a categorical outcome.

Another object of this invention is to provide a method for use in conjunction with one of several statistical techniques, such that panel constituents are not analyzed and/or compared merely on the basis of abnormalities, but also by consideration intra-panel constituent relationships.

Another object of the invention is to provide a method for use in conjunction with one of several statistical techniques, such that accuracy is increased by incorporation of non-constituent factors into the analysis and/or comparison.

Another object of the invention is to provide a method which permits adjustment of prior probabilities such that the analysis can be tailored to preferentially identify a particular consumption category.

Another object of the invention is to provide a method which permits adjustment of prior probabilities such that the analysis is tailored to preferentially minimize false positive identifications.

Another object of the invention is to provide a method for determining a category of alcohol consumption rate which accounts for inter-laboratory differences, equipment variations, and related analytic anomalies.

Another object of the invention is to provide a method for determining a category of alcohol consumption rate which involves, in part, correlation of subject and reference blood constituent panels with consumption rate categories derived from one of a variety of alcohol assessment standard instruments.

Other objects, features and advantages of the present invention will be apparent from the following summary, taken in conjunction with the accompanying examples, studies, figures and tables.

SUMMARY OF THE INVENTION

Figure 1:
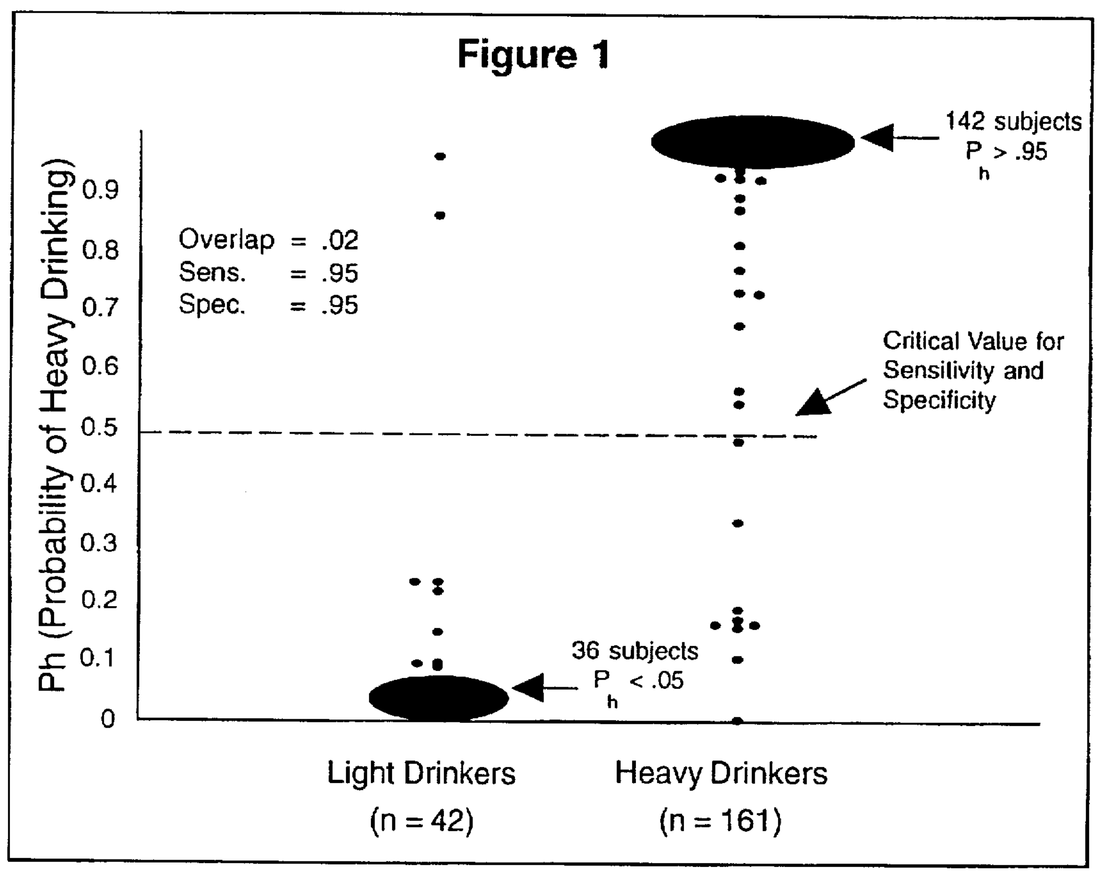
FIG. 1 illustrates the performance of the EDED of this invention, with respect to the validation data set.

This invention is an improved method for the assessment of alcohol consumption, which provides a means to evaluate and determine an individual's rate of alcohol intake, in a manner which minimizes false positive results without a necessarily concomitant loss in sensitivity. The method can be varied through modification of a statistical model used therewith to preferentially weigh the analysis and identify one consumption category over another. Multi-variate and similar such statistical techniques correlate comparisons of individual/subject blood and reference panel constituents with recognized consumption rate categories.

In accordance with the present invention, a method for assessing alcohol consumption rates includes (1) using a blood specimen from a human subject to develop an individual blood constituent panel, which has about at least ten constituents; (2) comparing the individual panel with a reference blood constituent panel to provide categories corresponding to rates of alcohol consumption; and (3) identifying the category of consumption rate for the subject indicated by the comparison. The reference blood constituent panel includes value ranges for the level of each constituent, whereby the relationship of one constituent to another can be determined. The reference panel is developed using a pool of human subjects and priority probability values corresponding to the likelihood that the subject would be classified in a particular category of alcohol consumption. A plurality of alcohol consumption categories are available for correlation to the reference panel, the number of categories depending upon the alcohol assessment standard instrument employed.

In preferred embodiments of the invention, three categories of alcohol consumption are used in conjunction with the reference panel. In highly preferred embodiments, a probability value of about 0.7–0.9 represents the lowest consumption rate; a probability value of about 0.08–0.20 represents the intermediate consumption rate; and a probability value of about 0.01–0.10 represents the highest consumption rate. The highest consumption rate is associated with the ratio of direct bilirubin concentration to total bilirubin concentration, a constituent used with one or both panels.

As mentioned above, consumption rate categories are derived from alcohol assessment standard instruments. Instruments useful with the present invention include psychological tests such as the Khavari Alcohol Test, the McAndrew scale, and MODCRIT. In highly preferred embodiments, the standard instruments are volume frequency alcoholism assessment tests.

The method of this invention can further include use of a statistical analysis which is modifiable to preferentially identified to one category of consumption rate over another. In preferred embodiments, the analysis is a multi-variate statistical technique. In highly preferred embodiments, the technique is selected from the group consisting of logistic regression, discriminant analysis, cluster analysis, factor analysis, and neuronetworking. The preferred technique includes standardization of individual/subject constituent panels through conversion of detected constituent levels to standard scores, to account for inter-facility/laboratory differences. The accuracy of the method is further increased where the individual and reference panels and statistical analysis incorporate such factors as age, gender, race, nationality, diet, geography, socioeconomic status, and drug interaction.

The method of this invention can include a second comparison of an individual panel with a reference panel having β-hexacosanamine (Betahex) such that the category of consumption rate can be identified without false positive results. Additional reference panel constituents includes selenium, carbohydrate deficient transferrin, and hemoglobin associated acetaldehyde, among others.

The present invention also includes a method for determining the approximate rate of alcohol consumption by a human test subject, having the steps (1) using a blood specimen from a subject to develop a subject blood constituent panel having at least 12 constituents, two of which are selected from the group consisting of high density lipoprotein, magnesium and the ratio of direct bilirubin to total bilirubin; (2) comparing the subject panel with a first reference constituent panel to provide categories corresponding to rates of alcohol consumption, the reference panel including two of high density lipoprotein, and magnesium, and the bilirubin ratio as constituents; (3) identifying the category of consumption rate for the subject indicated by the comparison; and (4) comparing, where the subject is identified with a particular category of alcohol consumption rate, the subject panel with a second reference constituent panel including β-hexacosanamine as an additional constituent, such that false positive results are minimized. The reference blood constituent panel includes value ranges corresponding to the level of each constituents, whereby the relationship of one constituent to another can be determined. The reference panel is developed using a pool of human subjects and prior probability values corresponding to the likelihood that the subject would be classified in a particular category of alcohol consumption. A plurality of alcohol consumption categories can be employed. In preferred embodiments, three categories of alcohol consumption, corresponding to increase consumption rates of alcohol per unit time, are used and associated with prior probability values of about 0.70–0.90 for that category reflecting the lowest consumption rate, about 0.08–0.20 for that category reflecting the intermediate consumption rate, and about 0.01–0.10 for that category reflecting the highest consumption rate. Increased consumption and the highest consumption rate is associated with the ratio of direct bilirubin to total bilirubin, a constituent useful in conjunction with one or both panels.

The categories of alcohol consumption are derived from alcohol assessment standard instruments. In preferred embodiments, the instruments are volume frequency alcoholism assessment tests. In highly preferred embodiments, the assessment tests are selected from the group consisting of the Khavari Alcohol Test, the McAndrew Scale, and MODCRIT.

The method of the invention can further include use of a statistical analysis modifiable to preferentially identify one category of consumption rate over another. In highly preferred embodiments, the analysis is a multi-variate statistical technique. In highly preferred embodiments, the technique is a statistical model such as logistic regression, discriminant analysis, cluster analysis, factor analysis, and neuronetworking. The accuracy of the method is enhanced by incorporating into the panels and statistical analysis factors such as age, gender, race, nationality, diet, geography, socioeconomic status and drug interaction.

As mentioned above and with general regard to the invention, the persons used to develop the reference panel of the present invention are preliminarily grouped into one of two classification variables related to alcohol consumption, i.e., abusive and non-abusive categories. Groups are derived through use of a psychological test, preferably selected from a group of such tests including the Khavari Alcohol Test, the McAndrew scale and MODCRIT. Of these, the Khavari Alcohol Test is a preferred assessment instrument.

The accuracy of the invention is improved where the reference panel is developed using a relatively large number of subjects—typically, at least several hundred subjects and preferably about 1200 or more subjects. The resulting reference blood serun panel may include any of the widely-recognized SMA 6, SMA 12 and Hematological constituents although other similar, common tests and their corresponding constituents may also be used to develop such a reference panel. Still other embodiments of the present method involve development of reference and individual/subject panels, ranges of age, individual/subject gender and like factors to further enhance accuracy.

As noted above, the present invention includes a method for determining an individual's alcohol consumption level based upon certain blood constituents (or variables as they are sometimes called) and upon the levels of such constituents compared to a reference. The constituents are collectively known as a panel i.e., a listing of constituents such as glucose, albumin, red blood count and the like which are present (as detected by lab laboratory analysis) in blood serum. For a given blood sample, each constituent is accompanied by an indication of the level of such constituent (usually per unit of volume) present in the sample. Of course, each constituent can—and does—vary from person to person and from time to time for a particular person. As a result, so-called normal ranges recognize the possibility of such variations. The reference panel includes not only the normal range of values for each serum constituent but also includes at least two other ranges for each constituent. These additional ranges relate to "heavy" and "very heavy" consumption rates of alcohol.

The reference and individual/subject panels include, alternatively, at least ten or at least twelve constituents, wherein two of the twelve are HDL and magnesium. But for the inclusion of HDL and magnesium with respect to the second alternative, the precise constituent makeup of either panel is not especially critical. For example, many laboratories offer blood serum analysis services and provide their own panel construction. A variety of blood serum constituents can comprise either panel, the identity and number of which are limited only by their response, and accuracy thereof to the general level of alcohol consumption, their relationship one to another, and the analytic capabilities of an individual laboratory. The constituent response to either alcohol consumption or to another constituent, is not necessarily linear and, in most instances, is distinctly non-linear. Constituents useful with the method of the present invention include but are not limited to neurophils-platelet type (BASO), calcium (Ca), chlorine (Cl), direct bilirubin (DBIL), lactose dehydrogenase (LDH), monophils-platelet type (MONO), sodium (Na), phosphorus (P), white blood count (WBC), copper (Cu), and zinc (Zn), among others. Blood constituents useful with the methods of this invention are generally alcohol-specific; that is, they are less affected by other events occurring in the body than they are by the level and/or rate of alcohol consumption.

One embodiment of the invention includes high density lipoprotein and magnesium as constituents. The blood serum level of HDL increases with heavy drinking while that of magnesium decreases. Selenium, copper and/or zinc are additional constituents. In general, the levels of selenium and zinc decline with heavy alcohol consumption, while the level of copper increases. Selenium is also useful as a constituent for the purpose of a second comparison of an individual panel with a reference panel to eliminate false positive results. Other constituents used with the same effect include β-hexacosanamine, carbohydrate deficient transferrin, and hemoglobin associated acetaldehyde. While the prior art uses the last two constituents as part of tests purporting to be alcohol markers, the present invention can utilize them much more effectively, not by themselves, but as a part secondary comparison or reflex test off the reference panel. Considerable cost savings are realized by using such constituents primarily to eliminate false positives from a given alcohol consumption category identified through an initial screening or comparison.

The reference panel used with a method of the invention is derived from persons, taken from populations having, by percent distribution, known drinking habits, grouped preliminarily into one of two classification variables, i.e., abusive, consumer and non-abusive consumer categories, using one of several available alcohol assessment standard instruments. Notwithstanding accepted test methodology, a formerly-abusive consumer is grouped into the non-abusive consumer category only if s/he had been abstinent for at least 8 weeks rather than the customary 2–3 weeks.

Preferred assessment instruments include psychological tests such as the Khavari Alcohol Test, the McAndrew scale and MODCRIT. Of this group, the Khavari test is most preferred. A feature of the Khavari test is that it elicits information from the subject which enables annual consumption rates of alcohol to be closely estimated. Annual consumption of ethanol is organized according to three groupings, one of which becomes the second classification variable described above. The Khavari test also includes check questions which aid greatly in assessing respondent veracity.

Under the constricts of the Khavari test, consumption of 0–590 oz. ethanol annually comprises Group 3, light-to-moderate; consumption of 591–1180 oz. annually comprises Group 2, moderate-to-heavy; consumption of more than 1180 oz. annually comprises Group 1, very heavy. The consumption rates represent one, two and more than two standard deviations above the mean, respectively.

After all alcohol consumers in the panel population are identified and categorized as described above, blood samples are taken from each person in each group and analyzed. Correlation of each sample (and its analysis) to the relevant group i.e., Group 3, 2 or 1, is maintained so that the reference norms are accurately related to the group responsible for the data.

Consistent with the comparative methodology of the invention, prior probability values can be assigned from categorization in Group 3, 2 or 1, and preferred values are between about 0.7 and 0.9, between about 0.08 and 0.20 and between about 0.01 and 0.10 for groups 3, 2 and 1, respectively. Within those ranges, prior probability values of about 0.86, 0.1 and 0.04, respectively, are highly significant. Such values correspond to the chances that a person belongs in a particular group, and are consistent with the level of alcohol consumption in the general population. Such values are useful in broad application of the present invention as a diagnostic tool by business, institutions and care providers.

The member panels comprising the reference blood serum panel can be treated with a multi-variate statistical technique to provide weighted values for each constituent of the reference panel. As shown in the Examples below, discriminant analysis is a preferred statistical technique, although others can be used with comparable results without deviating from the scope of this invention. Discriminant analysis can be performed through use and with the aid of the DISCRIM computer program, from the Statistical Package For Social Science (SPSS) PC+ statistical package available from SPSS, Inc. of Chicago, Ill. However, other statistical programs are also available for use with discriminant analysis, as well as with other statistical and/or multi-variate techniques suitable for use with the invention.

Discriminant analysis is a technique commonly used in the social sciences and less frequently in medicine. It is similar to logistic regression in that it can be used to predict a nominal or categorical outcome. Discriminant analysis differs from logistic regression in several ways; most importantly: it assumes that the independent variables follow a multi-variate normal distribution, so that it must be used with caution if some X variables are nominal; and it can be used with a dependent variable that has more than two values.

The procedure involves determining several discriminant functions, which are nothing more than linear combinations of the independent variables, that separate or discriminate among the groups to the extent possible. The number of discriminant functions needed can be determined by a multi-variate test statistic referred to as Wilks' Lambda. The discriminant functions' coefficients can be standardized, then interpreted in the same manner as with multiple regression to draw conclusions about which variables are important in discriminating among the groups. See, also, Dawson-Saunders and Trapp, *Basic and Clinical Biostatistics*, published by Appleton & Lange; and Altman, *Practical Statistics for Medical Research*, published by Chapman & Hall.

The result is a standardized (canonical discriminant functions' coefficients) reference blood serum panel which provides reference ranges for each constituent and for each of the three consumption levels, i.e., light-to-moderate, moderate-to-heavy and very heavy. A method consistent with the invention may further include gender, age and the like categories as additional variables to further enhance accuracy of the method. Typical age categories are 18–35, 36–64 and over 64 years of age. After the reference panel is developed, it is used in comparison with an individual/subject panel, which is preferably constructed like the reference panel, with respect to constituent composition. The individual/subject panel is then statistically analyzed against the reference panel, with the deviations noted.

As discussed above, heavy drinkers often deny the extent of their alcohol consumption. Commonly-used laboratory tests were evaluated to derive and assess an equation for use as an objective method to identify heavy drinkers. One thousand fifty-seven subjects were initially recruited for this effort. All subjects were paid volunteers recruited from the metropolitan area of Milwaukee, Wis. Sources of light drinkers included three primarily white, middle-class churches, an inner-city African-American church, three support groups of recovering alcoholics and drug abusers, a college campus, a golf outing, and a work setting. Some heavy drinkers were also recruited from these settings but most were recruited from detoxification centers and from an inner city area that is impoverished and has a high rate of alcoholism. The volunteers recruited from the inner city had responded to advertising on bulletin boards in a church with an active program for alcoholism and in several blood banks in the same area.

Data for the study were collected from Jun. 11, 1992 to Dec. 7, 1994 from 1057 paid volunteers who allowed a blood draw for laboratory tests and answered questionnaires. The 40 blood tests collected on all study patients are commonly performed laboratory tests relating to hematology, liver enzymes, lipids, electrolytes, and others. The specific tests are listed in Table C, below. All of the analyses for these 40 tests were performed by Roche Biomedical Laboratories in one of three locations (Northbrook, Ill.; Columbus, Ohio.; and Raritan, N.J.). Another laboratory, the Home Office Reference Laboratory in Kansas City, Kans., had an interest in evaluating three other tests that are specifically used to identify alcoholics: carbohydrate deficient transfenin (CDT), hemoglobin-associated acetaldehyde (HAA), and β-hexosamine. This laboratory performed the analysis on these three tests for 288 subjects recruited between Jun. 24, 1992 and Dec. 3, 1993. HAA was measured using high performance liquid chromatography with Gilson equipment; CDT was measured by radioimmunoassay.

From a general questionnaire information was obtained on the subjects' age, time since last drink, smoking history, and use of other chemical substances. The subjects also completed the Self-Administered Alcohol Screening Test (SAAST), a screen for problem drinking, and the Khavari questionnaire, a method to determine annual alcohol consumption. Subjects whose responses to the Khavari questionnaire indicated that they drank more than 700 ounces of alcohol during the past year were considered to be heavy drinkers; other subjects were considered to be light drinkers. Although no specific questionnaire information was obtained on socioeconomic status, heavy drinkers treated at the expense of the county or who were recruited from the inner city area described below were considered to be in the lower socioeconomic status group.

Only data from men were analyzed. Women were excluded because the relationships between laboratory test results and drinking status were found to differ significantly between men and women and there were insufficient numbers of women (n=339) to analyze separately in training and validation data sets. Men were excluded from the study for the following reasons: (1) 6 men said they were light drinkers but their answers on the SAAST questionnaire suggested that they may have had a drinking problem; (2) 18 heavy drinkers were excluded because they had levels of gamma glutamyl transferase (GGT) greater than 600 IU/L (about 9 times the upper limit of normal) and would have been identified as heavy drinkers with this single liver enzyme test that is frequently used as an indication of alcoholism; (3) 18 were excluded because of inadequate serum handling; and (4) 19 subjects were excluded because of missing data. No male heavy drinkers recruited from detoxification centers or the inner city drank less than 700 ounces of alcohol according to the Khavari questionnaire. After the exclusions 613 subjects remained for analysis.

The data were divided into two groups for analysis: (1) a training data set that was used to derive an equation for identifying heavy drinkers and (2) a validation data set that was used to evaluate the performance of this equation. The validation data set included all of the 171 men who had the results of the three alcohol specific laboratory tests: HAA, CDT, and β-hexosamine. Including these subjects in the validation data set permitted the performance of the three tests to be compared to the performance of the equation derived in the training data set. The validation data set also included all 32 subjects recruited after Mar. 30, 1994 through Dec. 17, 1994. All other subjects were included in the training data set.

All statistical analyses were performed using the well-known and available Stata statistical package. The relationship between the results of a single laboratory test and heavy drinking was evaluated with a t-test. The relationship of a set of laboratory tests with heavy drinking was examined with logistic regression analysis. The logistic regression equation found with this analysis expresses the functional relationship between the values of the laboratory tests and the probability that a person is a heavy drinker. The logistic regression equation is $$p=1/(1+e^{-(a+x_1b_1+x_2b_2+\ldots)})$$

where p is the probability that a subject is a heavy drinker, $x_1$ is the value of the laboratory test and $b_1$ is the coefficient for the values of that laboratory test. The statistical program estimates where p is the probability that a subject is a heavy drinker, $x_i$ is the value of the i-th laboratory test and $b_i$ is the coefficient of that laboratory test. The statistical program estimates the values of the coefficients to give probabilities that best fit the data.

All laboratory tests were candidates for the final regression equation. Age was also considered for the equation since the results of some laboratory tests change with age. To reduce the number of variables in the equation, forward and backward stepwise logistic regression procedures and the best linear regression equation were used. Any of the variables selected with these methods were then included in a backwards stepwise regression analysis. This final backwards stepwise logistic regression procedure eliminated all variables not significant at the p<0.01 level. The regression equation derived with this procedure will be referred to as the Equation to Detect Excess Drinking or EDED.

Once the variables to be included in EDED were determined, the following transformations of these variables were tested as to whether they might improve the equation: the logarithmic, reciprocal, quadratic, square root. The interaction among the variables was also tester; i.e., whether the influence of one variable on the probability of being a heavy drinker was affected by the value of other variables.

The strength of association of each variable in the EDED with heavy drinking is presented as the relative odds associated with an increase in the variable of one quarter of the normal range for that variable as determined by Roche Biomedical Laboratories. Roche Laboratories defined the normal range as the mean plus or minus 1.96 standard deviations for all of the laboratory variables that had a normal distribution in an apparently well ambulatory population. If the variable did not have an approximately normal distribution, the normal range was determined by Roche Laboratories using nonparametric methods to estimate the 95% confidence interval.

The EDED was evaluated in the validation data. For this evaluation the sensitivity, specificity, and overlap index were used to measure how well the EDED score (i.e., the probability that a person was a heavy drinker based on the EDED) discriminated between heavy and light drinkers in the validation data set. The sensitivity of EDED was defined as the proportion of all heavy drinkers who had an EDED score of greater than 50%, and specificity was defined as the proportion of all light drinkers who had an EDED score of less than 50%. The overlap index is mathematically equivalent to several other statistics that can be used to measure the performance of a prediction equation including the area under the Receiver Operator Characteristic (ROC) curve, the C statistic and the Somers' D. The overlap index was used because it is intuitively easy to understand. The overlap index would be 0.0 if the EDED score is greater for each heavy drinker than for all light drinkers. It would be 1.0 if the average rank of the EDED scores are the same for the heavy and light drinkers.

The sources for the subjects analyzed are shown in Table A. Many of the heavy drinkers admitted to other substance abuse: primarily cocaine (n=236), marijuana (n=187), and heroin (n=5). Some middle class volunteers were found to be heavy drinkers. Only seven light drinkers admitted to other substance abuse.

The demographic characteristics of the study population are shown in Table B. In both the training and the validation samples heavy drinkers are younger than light drinkers and more likely to be African Americans. The heavy drinkers were significantly less likely to be white in the validation than in the training data set (p=0.002), and the light drinkers were more likely to be older (p=0.07) and more likely to be white (p<0.001) in the validation than in the derivation data. An equation derived in a sample more similar to the validation data set should perform better in the validation data than the equation derived in this training set.

The association of the results of the individual laboratory tests with heavy drinking is shown in Table C. For most tests the association was statistically significant, and for many tests the association was significant at the p<0.0001 level. The t-values for the most statistically significant tests were 9.08 for the percentage of white blood cells that were monocytes, −6.85 for sodium, 6.80 for gamma glutamyl transferase (GGT), and 5.01 for chloride levels. All of these t-values are statistically significant at the p<0.0001 level. The t-value was much lower for the mean corpuscular volume which is often considered to be an important diagnostic tool for alcoholism. In our data the differences in the mean corpuscular volume between heavy and light drinkers was much greater for Whites (95.3 fl vs. 90.9 fl, $p<0.0001$), than for African Americans (91.6 fl vs. 89.3 fl, $p<0.01$).

As shown under the section on liver tests the heavy drinkers were found to have substantially higher values of direct bilirubin than the light drinkers even though the total bilirubin was slightly lower. For this reason another variable was devised: the ratio of direct to total bilirubin. Heavy drinking had a much stronger association with this variable ($t=13.3$, $p<0.0001$) than it did with direct bilirubin ($t=6.5$, $p<0.0001$).

The variables included in the best logistic regression equation (the EDED) are shown in Table D. All of the variables in the EDED, except the platelet count, were associated with heavy drinking at the $p<0.0001$ level in the univariate analysis presented in Table C. There were an additional 16 laboratory tests that were also associated with heavy drinking at the $p<0.0001$ level in univariate tests but after adjusting for other variables were not significant and therefore were not included in the EDED. The equation was not improved using any of the variable transformations discussed in the methods section. No interaction terms were statistically significant at the $p<0.01$ level. Even though race was highly associated with heavy drinking in a univariate analysis ($p<0.0005$ using a chi-squared contingency table test), it was not a statistically significant variable after adjusting for the other laboratory values.

Table D includes the regression coefficient, relative odds, and statistical significance for each variable. Since the results are from a multiple logistic regression analysis, the p value and relative odds for each of the variables represent the independent association of a given laboratory test with drinking status after adjusting for all of the other variables in the logistic regression equation. The variables are divided into those that increase and those that decrease in heavy drinkers after adjusting for the other variables. Within each group the variables are listed in order of decreasing statistical significance; i.e., chloride is the most statistically significant variable that increases the risk of being a heavy drinker ($p<0.0005$), and phosphorus and mean corpuscular hemoglobin are the least statistically significant variables that increase the risk of being a heavy drinker ($p=0.005$). One of the variables in the equation with the strongest association with heavy drinking was the ratio of the direct to the total bilirubin. The t-value for this variable was 4.54 compared to a t-value of 1.16 if the direct bilirubin was substituted for the ratio. The normal range of this ratio was not available from Roche Biomedical Laboratories. Therefore, to compute the relative odds the standard deviation of the ratio for light drinkers in the combined training and validation data sets were used.

Sodium is the most statistically significant variable that decreases the relative odds. Although its association with heavy drinking is in the opposite direction of chloride's, it has a high positive correlation with chloride ($r=0.54$). No other variables in the EDED have correlations above 0.40.

The value of the overlap index for the EDED is almost zero (0.017) indicating that in the training data almost all heavy drinkers have a higher EDED score probability of being a heavy drinker) than almost all of the light drinkers. However, since the logistic regression equation was derived to fit the data, the performance of the equation in this data set is better than it will be in other data sets.

The performance of the EDED in the validation data set is shown in FIG. 1. In this FIGURE the EDED scores are shown for the light drinkers and for the heavy drinkers. The scores were greater than 0.95 for 88% (142) of the 161 heavy drinkers and less than 0.05 for 84% (36) of the 42 light drinkers. Only one of the 145 subjects with the highest scores (>0.90) was a light drinker, and only one of the 39 subjects with the lowest scores ($\leq 0.10$) was a heavy drinker. Because there was little overlap in the EDED scores between the heavy and light drinkers, the overlap index was 0.022. If 50% was used as a cut off score to identify heavy drinkers, the sensitivity of EDED was 95%, the specificity was 95%, and only 10 of the 203 subjects in the validation data were misclassified.

The ability of an abnormal value of each individual test in the EDED to identify heavy drinkers is shown in Table E. Although some of the tests are much more likely to be abnormal for heavy than for light drinkers, only the ratio of direct to total bilirubin had a moderately high sensitivity.

As described above, Table A shows that age and race are confounded with heavy drinking. In Table F the possible effect of this confounding was examined. The table included both subjects in the training and validation data sets so that the sample size would be larger in the subgroups evaluated. When all subjects were considered, the mean EDED score for heavy drinkers, 0.95, is much larger than for the light drinkers, 0.09. Compared to African American subjects, white subjects have a lower mean EDED score, a lower sensitivity, and a higher specificity. However, the sensitivity and the specificity are high for both Whites and African Americans. Age did not affect the results for either race.

The demographic factor with the strongest influence on the EDED score was insurance status, a marker for socioeconomic status. Heavy drinkers who were insured had a lower EDED score than uninsured subjects. The EDED score for White and African American heavy drinkers are similar if the insurance status is the same. Therefore, it is likely that socioeconomic status rather than race is the reason for differences in EDED scores between Whites and African Americans.

Although smoking is not a demographic factor, it is a possible confounder for this study since 84% of the heavy drinkers but only 30% of the light drinkers were smokers. The mean EDED seemed to be unaffected by smoking status as shown in Table 6 and both the sensitivity and specificity were high after dividing subjects into groups on the basis of smoking. For heavy but not for light drinkers, smokers had higher EDED scores than nonsmokers. This suggests that smoking does not directly affect the laboratory results, but heavy drinkers who smoke may drink more than heavy drinkers who do not smoke. The use of cocaine or marijuana are also possible confounders in this study, but neither were associated with significantly higher EDED scores for the heavy drinkers.

To evaluate the duration of the effects of heavy drinking on laboratory results, persons who had not had a drink for at least one week were examined, as were recovering alcoholics. There were 15 heavy drinkers whose last drink was one week to one month prior to being tested (mean EDED score=0.88) and one heavy drinker whose last drink was 13 weeks prior to being tested (EDED score=0.79). Six of these 16 subjects were insured and may have had lower probabilities for this reason. For all 16 subjects the EDED had a sensitivity of 94%. The mean EDED score of the recovering alcoholics was 0.13 and the specificity of the EDED for this group of light drinkers was 91%. Half of these subjects had not had a drink for at least 61 months and 90% had not had a drink for at least nine months. These results suggest that the effects of alcohol on laboratory tests last longer than a week, but eventually return to normal.

The association between the probabilities of heavy drinking and the source of the subjects as listed in Table A for all subjects combined was also examined. The mean value for light drinkers ranged from 0.04 for the various middle class groups to 0.10 for the church group. The variation according to source of subjects for light drinkers was not statistically significant using a one-way analysis of variance ($p=0.10$ for 189 subjects in 3 groups). For heavy drinkers the means ranged from 0.71 for the middle class groups to 0.99 for the inner city group. The variation according to source of subjects for heavy drinkers was statistically significant before adjusting for insurance status (p<0.0001) but not after (p=0.29 for 425 subjects in 3 groups).

The results of three tests frequently used to identify alcoholics (carbohydrate deficient transferrin, hemoglobin-associated acetaldehyde, and β-hexosamine) were compared to the results of EDED in Table G. Data on the

TABLE A

| | Number of Subjects According to Source of Data | | | |
|---|---|---|---|---|
| | Training | | Validation | |
| Source of Data | Heavy | Light | Heavy | Light |
| Detox Centers | 248 | 0 | 65 | 0 |
| Inner City | 15 | 0 | 90 | 0 |
| Recovery Groups | 0 | 61 | 0 | 0 |
| Churches | 0 | 70 | 0 | 21 |
| Various Middle Class Groups | 1 | 15 | 6 | 22 |

TABLE B

| | Patient Demographic Characteristics | | | |
|---|---|---|---|---|
| | Training Data Set | | Validation Data Set | |
| | Heavy (n = 264) | Light (n = 146) | Heavy (n = 161) | Light (n = 43) |
| Age (Mean) | 36.8 | 41.5 | 36.0 | 45.4 |
| Race | | | | |
| White | 30% | 70% | 18% | 98% |
| African-american | 65% | 29% | 81% | 2% |
| Other | 5% | 1% | 1% | 0% |

All differences between heavy and light drinkers is each data set are statistically significant at the p>0.0001 level.

TABLE C

| Mean Values for Laboratory Tests | | | | | |
|---|---|---|---|---|---|
| Laboratory Test | Heavy Drinkers (n = 264) | Light Drinkers (n = 146) | Laboratory Test | Heavy Drinkers (n = 264) | Light Drinkers (n = 146) |
| Hematology | | | Globulin (g/dl) | 3.0 | 3.1 |
| Red blood cells* (× $10^3$/ul) | 4.8 | 5.0[c] | Albumin* (g/dl) | 4.2 | 4.4[c] |
| Hemoglobin* (g/dl) | 15.1 | 15.3 | Albumin/Globulin | 1.42 | 1.42 |
| Hematocrit* (%) | 44.1 | 45.3[a] | Lipids | | |
| Mean corpuscular volume* (fl) | 92.9 | 90.4[c] | High density lipoprotein* (mg/dl) | 56.0 | 39.3[c] |
| Mean corpuscular hemoglobin* (pg) | 31.7 | 30.6[c] | Low density lipoprotein (mg/dl) | 111.9 | 130.7[c] |
| Mean corpuscular hemoglobin | 34.2 | 33.8[c] | Very low density lipoprotein | 24.9 | 31.3[c] |
| concentration* (g/dl) | (mg/dl) | | | | |
| Platelets (× $10^3$/ul) | 249.0 | 241.9 | Cholesterol* (mg/dl) | 194.0 | 202.6 |
| White blood cells* (× $10^3$/ul) | 6.9 | 6.8 | Triglyceride* (mg/dl) | 136.1 | 178.1[c] |
| Polymorphonuclear leukocytes (%) | 53.5 | 58.2[c] | Renal Function | | |
| Lymphocytes (%) | 35.7 | 33.4[a] | BUN* (mg/dl) | 12.0 | 15.2[c] |
| Monocytes (%) | 7.6 | 5.4[c] | Creatinine* (mg/dl) | 1.06 | 1.13[c] |
| Eosinophils (%) | 2.7 | 2.4 | Bun/creatinine ratio | 11.1 | 13.3[c] |
| Basophils (%) | 0.54 | 0.42 | Electrolytes | | |
| Red cell distribution width (%) | 13.4 | 13.9[b] | Magnesium (mEq/L) | 1.7 | 1.8[c] |
| Liver Tests | | | Calcium* (mg/dl) | 9.7 | 9.9[c] |
| Direct bilirubin (mg/dl) | 0.22 | 0.14[c] | Phosphorus* (mg/dl) | 4.0 | 3.5[c] |
| Total bilirubin* (mg/dl) | 0.55 | 0.60 | Sodium* (mEq/L) | 138.8 | 140.5[c] |
| Direct/Total bilirubin (%) | 40.6 | 25.8[c] | Potassium* (mEq/L) | 4.3 | 4.3 |
| Lactic dehydrogenase* (IU/L) | 176.6 | 178.4 | Chloride* (mEq/L) | 104.1 | 102.5[c] |
| Aspartate aminotransferase* (IU/L) | 46.1 | 22.2[c] | Miscellaneous | | |
| Gamma glutamyl transferase* (IU/L) | 105.0 | 31.1[c] | Glucose* (mg/dl) | 99.8 | 97.3 |
| Alanine aminotransferase* (IU/L) | 39.7 | 21.4[c] | Iron (μg/dl) | 110.3 | 95.5[a] |
| Alkaline phosphatase* (IU/L) | 102.6 | 95.2 | Uric acid* (mg/dl) | 4.4 | 5.2[c] |
| Total protein* (g/dl) | 7.3 | 7.5[a] | Body mass index (kg/$m^2$) | 25.2 | 27.8[c] |
| | | | Age (years) | 37.1 | 41.5[c] |

*The variable is significant in at least 2 previously published studies of the association between alcohol and laboratory results.
[a]$p \leqq .01$
[b]$p \leqq .001$
[c]$p < .0001$

TABLE D

Variables in the Best Logistic Regression Equation (the EDED)

| Laboratory Test | Regression Coefficient | Relative Odds[d] | T-Value |
|---|---|---|---|
| Result Higher in Heavy Drinkers | | | |
| Chloride (mEq/L) | 0.88 | 27.1 | 5.22[c] |
| Bilirubin ratio[e] | 0.16 | 3.5 | 4.57[c] |
| Monocytes (%) | 0.9 | 4.8 | 4.21[c] |
| High density lipoproteins (mg/dl) | 0.12 | 2.9 | 4.06[c] |
| Aspartate aminotransferase (IU/L) | 0.09 | 3.1 | 3.20[b] |
| Platelets (× $10^3$/ul) | 0.02 | 3.8 | 3.02[a] |
| Phosphorus (mg/dl) | 1.39 | 2.0 | 2.84[a] |
| Mean corpuscular hemoglobin (pg) | 0.55 | 2.3 | 2.81[a] |
| Result Lower in Heavy Drinkers | | | |
| Sodium (mEq/L) | −1.21 | .020 | −5.04[c] |
| Blood urea nitrogen (mg/dl) | −0.35 | .190 | −3.79[c] |
| Age (five years) | −0.09 | .638 | 3.02[a] |

[a]p ≦ .01
[b]p ≦ .001
[c]p ≦ .0001
[d]based on increase of one quarter of the normal range
[e]direct/total bilirubin

TABLE E

Percentage of Patients with Abnormalities in the Individual Tests that are Part of EDED

| Test | Percent Abnormal: Heavy Drinkers (n = 161) | Light Drinkers (n = 43) |
|---|---|---|
| Results Higher in Heavy Drinkers* | | |
| Bilirubin ratio[b] | 69% | 0% |
| Chloride | 10% | 2% |
| Monocytes | 10% | 2% |
| High density lipoproteins[b] | 29% | 2% |
| Aspartate aminotransferase[a] | 17% | 2% |
| Platelets | 1% | 0% |
| Phosphorus | 14% | 9% |
| Mean corpuscular hemoglobin | 24% | 12% |
| Results Lower in Heavy Drinkers# | | |
| Sodium | 2% | 0% |
| BUN | 2% | 0% |

*Tests results are considered abnormal only if they are above the normal range.
Test results are considered abnormal only if they are below the normal range
[a]p < .01 for the difference in percentages between heavy and light drinkers
[b]p < .001

TABLE F

Performance of EDED According to Characteristics of the Subjects

| | Mean Probability: Heavy Drinkers | Light Drinkers | Sensitivity in Heavy Drinkers | Specificity in Light Drinkers |
|---|---|---|---|---|
| All subjects | .95 (n = 425) | .09 (n = 189) | 96% (n = 425) | 95% (n = 189) |
| White | .90 (n = 109) | .07 (n = 144) | 91% (n = 109) | 97% (n = 144) |
| African-american | .97 (n = 301) | .14 (n = 43) | 98% (n = 301) | 91% (n = 43) |

TABLE F-continued

Performance of EDED According to Characteristics of the Subjects

| | Mean Probability: Heavy Drinkers | Light Drinkers | Sensitivity in Heavy Drinkers | Specificity in Light Drinkers |
|---|---|---|---|---|
| White age 35 and over | .90 (n = 73) | .07 (n = 112) | 89% (n = 73) | 96% (n = 112) |
| Black age 35 and over | .97 (n = 148) | .13 (n = 30) | 99% (n = 148) | 93% (n = 300) |
| Uninsured white+ | .96 (n = 73) | — | 99% (n = 73) | — |
| Uninsured African-american+ | .98 (n = 289) | — | 99% (n = 289) | — |
| Insured white+ | .76 (n = 36) | — | 75% (n = 36) | — |
| Insured African-american+ | .81 (n = 12) | — | 83% (n = 12) | — |
| Smokers | .96 (n = 358) | .07 (n = 57) | 97% (n = 358) | 98% (n = 57) |
| Non-smokers | .87 (n = 41) | .10 (n = 127) | 85% (n = 41) | 94% (n = 127) |
| Last drink ≧ 1 week | .88 (n = 16) | — | 94% (n = 16) | — |
| Recovering alcoholics | — | .13 (n = 44) | — | 91% (n = 44) |

+Neither insurance status nor other indicator of socioeconomic level were available for light drinkers.

TABLE G

Performance of Measures used to Discriminate Between Light and Heavy Drinkers

| | Sensitivity (n = 139) | Specificity (n = 32) | Overlap Index |
|---|---|---|---|
| Hemoglobin associated acetaldehyde | 36% | 94% | 0.32[b] |
| Carbohydrate deficient transferrin | 40% | 94% | 0.70[a] |
| Beta hexosamine | 32% | 94% | 0.63[a] |
| EDED | 98% | 94% | 0.009[b] |

[a]p ≦ .01
[b]p ≦ .001 results of the three additional tests were only available for 171 subjects, 139 heavy drinkers and 32 light drinkers. All of the tests had an association with heavy drinking that was statistically significant at the p<0.01 level. For each test the threshold for identifying alcoholics was set sufficiently high that only two of the 32 light drinkers would be above the threshold; i.e., the specificity was 94%. With the threshold set in this way the sensitivity of EDED was 98% compared to 36% for hemoglobin-associated acetaldehyde, 40% for carbohydrate deficient transferrin, and 32% for β-hexosamine. The superior performance of EDED was also evident in its low overlap index which was only 0.009 in this data set compared to values for the other tests ranging from 0.32 to 0.70.

It is interesting to note that, with one exception, previous studies have not used the results of differential white blood cell counts, and no previous studies have used the ratio of direct bilirubin concentration to total bilirubin concentration. Likewise, it appears the scientific literature has no explanation for the association of heavy drinking with increased platelet counts or with the aforementioned bilirubin ratio. Without limiting the scope of the present invention or without advancing any one theory or explanation, the high bilirubin ratio observed in alcoholics may suggest that alcohol induces the uridine diphosphoglucuronosyl transferase liver enzyme. The present invention also contemplates the correlation or association of other tests, constituents, and/or factors with one or more possible categories of alcohol consumption.

EXAMPLES OF THE INVENTION

The following non-limiting examples illustrate use of methods and identification of consumption levels, in accordance with the present invention. Comparisons of multiple individual/subject panels against a reference panel were simulated by random choice of a large member of individual data sets from a larger reference pool. Using this database (292, Examples 1 and 2; and 248, Example 3) 80% of the panels (240, Examples 1 and 2; and 196, Example 3) were randomly selected to comprise reference norms (a different 240 for each of Examples 1 and 2), such that the remaining 20% of each served as a validation group of unknowns with which to evaluate the methodology employed. Comparison of the consumption category identified through use of a particular method with the category known for each individual panel of the validation group gave the percent correctly classified, as well as the false negatives and false positives.

EXAMPLE 1

Using a 10-constituent panel and prior probabilities of 0.3 and 0.7, the data sets of 292 males under age 36 were chosen, of which 240 comprised the reference panel and 52 were randomly selected, as described above. As shown in Tables 1a–1c and well-known to those skilled in the art and made aware of this invention, the discriminant functions were determined, with the coefficients standardized and assigned weighted values. Constituent levels are either directly or inversely proportional to consumption rates. A significance of 0.000 indicated that the odds the conclusions drawn about variables in discriminating among groups and the categorical outcome determined were the result of chance are less than one in ten thousand. In Table 1d the functions are evaluated at group means. The clustered array of group 1 centroids about 0.46860 and group 2 centroids about −1.96610 denotes a high degree of accuracy. One hundred percent of the non-abusive consumers and 79.1% of the abusive consumers were correctly identified, as a result of this analysis and subsequent comparison. Overall, 82.7% of the group cases were correctly identified, with zero false positive identifications.

TABLE 1a

| Prior probabilities Group | Prior | Label |
|---|---|---|
| 1 | .30000 | Abusive |
| 2 | .70000 | Non-abusive |
| Total | 1.00000 | |

Canonical Discriminant Functions

| Fcn | Eigenvalue | Pct of Variance | Cum Pct | Canonical Corr | After Fcn | Wilks' Lambda | Chi-square | df | Sig |
|---|---|---|---|---|---|---|---|---|---|
| | | | | | 0 | .518377 | 152.436 | 10 | .0000 |
| 1* | .9291 | 100.00 | 100.00 | .6940 | | | | | |

*Marks the 1 canonical discriminant functions remaining in the analysis

TABLE 1b

Standardized canonical discriminant function coefficients

| | Func 1 |
|---|---|
| BASO | .16941 |
| CA | −.20721 |
| CL | .70725 |
| DBIL | .19026 |
| HDL | .49681 |
| LDH | −.37079 |
| MONO | .49334 |
| NA | −.64226 |
| P | .24934 |
| WBC | .45374 |

TABLE 1c

Structure matrix:
Pooled within-groups correlations between discriminating variables and canonical discriminant functions
(Variables ordered by size of correlation within function)

| | Func 1 |
|---|---|
| HDL | .38860 |
| MONO | .38135 |
| P | .31358 |
| CA | −.31146 |
| CL | .26174 |
| DBIL | .23827 |
| NA | −.23366 |
| BASO | .12925 |
| LDH | −.10747 |
| WBC | .07452 |

TABLE 1d

Canonical discriminant functions evaluated at group means (group centroids)

| Group | Func 1 |
|---|---|
| 1 | .46860 |
| 2 | −1.96610 |

Symbols used in plots

| Symbol | Group | Label |
|---|---|---|
| 1 | 1 | Abusive |
| 2 | 2 | Non-Abusive |
| # | | All ungrouped cases |

All-groups Stacked Histogram
Canonical Discriminant Function 1

```
           32 ┤
              │
              │
           24 ┤                        1
              │                        1
Frequency     │                      #  1 1
              │                      2 11 1
           16 ┤                      1 1111
              │                      1 11111
              │                     11111111     1
              │                2    11111111     1
            8 ┤               22 2 1111111111   11
              │              2222121111111111   11
              │          2  222111111111111111  11
              │          22222111111111111111   111 1
              │      22222222221111111111111111111111111    1
              X ──────┼──────┼──────┼──────┼──────┼────── X
            out     -4.0   -2.0     .0     2.0    4.0     out
Class       2222222222222222222222222222221111111111111111111111111111111
Centroids                   2         1
```

EXAMPLE 2

TABLE 1e

Classification results for cases selected for use in the analysis -

| Actual Group | | No. of Cases | Predicted Group Membership 1 | Predicted Group Membership 2 |
|---|---|---|---|---|
| Group Abusive | 1 | 193 | 154<br>79.8% | 39<br>20.2% |
| Group Non-abusive | 2 | 46 | 2<br>4.3% | 44<br>95.7% |
| Ungrouped cases | | 1 | 1<br>100.0% | 0<br>0% |

Percent of "grouped" cases correctly classified: 82.85%

Classification results for cases selected for use in the analysis

| Actual Group | | No. of Cases | Predicted Group Membership 1 | Predicted Group Membership 2 |
|---|---|---|---|---|
| Group Abusive | 1 | 43 | 34<br>79.1% | 9<br>20.9% |
| Group Non-abusive | 2 | 9 | 0<br>.0% | 9<br>100.0% |

Percent of "grouped" cases correctly classified: 82.69%

As shown in Tables 2a–d and as described above, the discriminant functions were again determined with the coefficients standardized and assigned weighted values. A 10-constituent panel was again employed, with prior probabilities of 0.5 and 0.5 such that the analysis was weighted or slanted toward a population having a higher number of problem consumers, and away from sociological norm. The data sets of the same 292 males under age 36 were again chosen, of which 240 comprised the reference panel and 52 were randomly selected, with the result being that random selection produced a different group of 52 than that used for validation purposes in Example 1. Again, a significance of 0.0000 showed the analysis highly unlikely to be the result of chance. Subsequent comparison correctly identified 100% of the non-abusive consumers and 90.7% of the abusive consumers, with 92.3% overall correct identification and zero false positives.

TABLE 2a

Prior probability for each group is .5000
Canonical Discriminant Functions

| Fcn | Eigenvalue | Pct of Variance | Cum Pct | Canonical Corr | After Fcn | Wilks' Lambda | Chi-square | df | Sig |
|---|---|---|---|---|---|---|---|---|---|
| 1* | .9291 | 100.00 | 100.00 | .6940 | 0 | .518377 | 152.436 | 10 | .0000 |

*Marks the 1 canonical discriminant functions remaining in the analysis.

TABLE 2b

Standardized canonical discriminant function coefficients

| | Func 1 |
|---|---|
| BASO | .16941 |
| CA | −.20721 |
| CL | .70725 |
| DBIL | .19026 |
| HDL | .49681 |
| LDH | −.37079 |
| MONO | .49334 |
| NA | −.64226 |
| P | .24934 |
| WBC | .45374 |

TABLE 2c

Structure matrix:
Pooled within-groups correlations between discriminating variables and canonical discriminant functions
(Variables ordered by size of correlation within function)

| | Func 1 |
|---|---|
| HDL | .38860 |
| MONO | .38135 |
| P | .31358 |
| CA | −.31146 |
| CL | .26174 |
| DBIL | .23827 |
| NA | −.23366 |
| BASO | .12925 |
| LDH | −.10747 |
| WBC | .07452 |

TABLE 2d

| Group | Func 1 |
|---|---|
| 1 | .46860 |
| 2 | −1.96610 |

Symbols used in plots

| Symbol | Group | Label |
|---|---|---|
| 1 | 1 | Abusive |
| 2 | 2 | Non-Abusive |
| # | | All ungrouped cases |

All-groups Stacked Histogram
Canonical Discriminant Function 1

```
          32 -
                                        1
          24 -                          1
                                      #  1 1
Frequency                             2 11  1
                                      1 1111
          16 -                        1 11111
                                     11111111      1
                                 2   11111111      1
                                22 2 1111111111   11
                               2222121111111111111 11
                           2 2221111111111111111111 11
                           2222211111111111111111111 111 1
                       22222222221111111111111111111111111111      1
               X ---------+---------+---------+---------+---------+--------- X
              out       -4.0      -2.0       .0        2.0       4.0       out
Class          2222222222222222222222222221111111111111111111111111111111111111
Centroids                           2          1
```

TABLE 2e

Classification results for cases selected for use in the analysis -

| Actual Group | | No. of Cases | Predicted Group Membership 1 | 2 |
|---|---|---|---|---|
| Group Abusive | 1 | 193 | 167<br>86.5% | 26<br>13.5% |
| Group Non-abusive | 2 | 46 | 3<br>6.5% | 43<br>93.5% |
| Ungrouped cases | | 1 | 1<br>100.0% | 0<br>.0% |

Percent of "grouped" cases correctly classified: 87.87%

Classification results for cases selected for use in the analysis

| Actual Group | | No. of Cases | Predicted Group Membership 1 | 2 |
|---|---|---|---|---|
| Group Abusive | 1 | 43 | 39<br>90.7% | 4<br>9.3% |
| Group Non-abusive | 2 | 9 | 0<br>.0% | 9<br>100.0% |

Percent of "grouped" cases correctly classified: 92.31%

Comparing Example 1 (prior probabilities of 0.3 and 0.7) and Example 2 (prior probabilities of 0.5 for each group) it is observed that a statistical analysis used in conjunction with a method of this invention can be modified to preferentially identify one category of consumption rate over another. While false positives were eliminated in each, the former was somewhat less sensitive. For certain uses and/or applications, such a decrease in sensitivity is acceptable where the prime consideration is the elimination of false positive results. As such, where identification of only those having alcoholic tendencies is required (for instance, prior probabilities of about 0.1 and 0.9) a slight decrease in sensitivity is acceptable so long as false positive indications are eliminated.

As noted above, the elimination of false positives is useful since blood serum analyses are often performed as part of, for example, a job application. The absence of false positives helps assure a user of the method that test results will not falsely indicate a person has a high rate of consumption when, in fact, s/he does not. Risk of loss of a job opportunity for reasons relating to alcohol consumption are thereby avoided.

EXAMPLE 3

Another method in accordance with the present invention is illustrated below, with the comparisons made using the statistical analysis described in Examples 1 and 2. A reference panel of twelve constituents, including high density lipoprotein and magnesium, was formed by random selection of 80% of a selected number of cases, with the remainder (20%) as a validation group representing unknown individuals. Accuracy is, again denoted as above, with the tight cluster of centroids shown in Table 3a. The results show 90% (38 of 42) of the abusive drinkers were correctly identified in the validation group, with 20% (2 of 10) false positives; see Table 3b. To eliminate false positive results, all subjects which were identified as abusive drinkers (38 from Group 1 and 2 from Group 2) were retested and compared to a reference panel which included β-hexacosanamine (Betahex) as an additional constituent. Accuracy was again evident, as illustrated in Table 3b. Through the additional comparison/reflex test, 84% of the abusive consumers were correctly identified, with 0% false positives; see Table 3d. In a similar fashion, additional constituents such as selenium, hemoglobin associated acetaldehyde, and carbohydrate deficient transferrin can also be used as additional/reflex test constituents for the purpose of identifying a particular consumption category without false positive results.

TABLE 3a

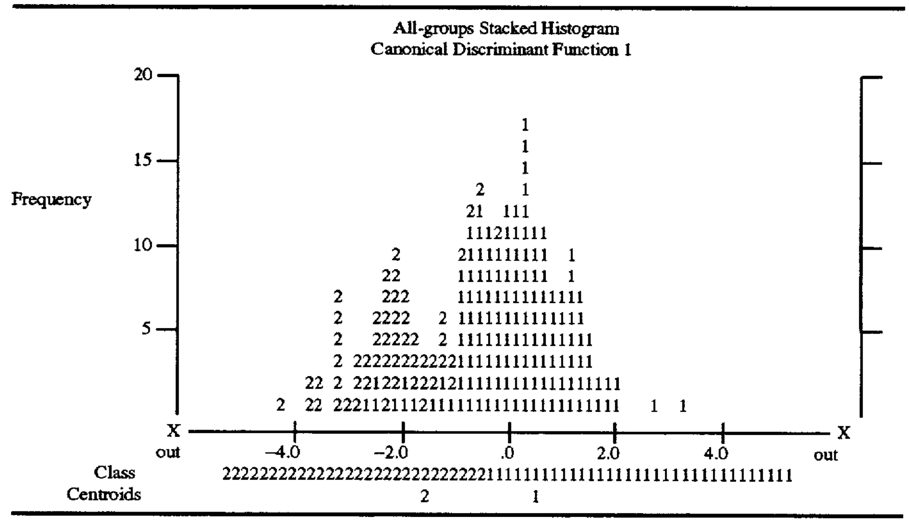

TABLE 3b

Classification results for cases selected for use in the analysis -

| Actual Group | | No. of Cases | Predicted Group Membership 1 | 2 |
|---|---|---|---|---|
| Group | 1 | 134 | 126<br>94.0% | 8<br>6.0% |
| Group | 2 | 61 | 3<br>4.9% | 58<br>95.1% |

TABLE 3b-continued

Classification results for cases selected for use in the analysis -

| Actual Group | | No. of Cases | Predicted Group Membership 1 | Predicted Group Membership 2 |
|---|---|---|---|---|
| Ungrouped cases | | 1 | 1<br>100.0% | 0<br>.0% |

Percent of "grouped" cases correctly classified: 94.36%
Classification results for cases selected for use in the analysis

| Actual Group | | No. of Cases | Predicted Group Membership 1 | Predicted Group Membership 2 |
|---|---|---|---|---|
| Group | 1 | 42 | 38<br>90.5% | 4<br>9.5% |
| Group | 2 | 10 | 2<br>20.0% | 8<br>80.0% |

Percent of "grouped" cases correctly classified: 88.46%

| Actual Group | | No. of Cases | Predicted Group Membership 1 | Predicted Group Membership 2 |
|---|---|---|---|---|
| Group | 1 | 38 | 35<br>92.1% | 3<br>7.9% |
| Group | 2 | 2 | 0<br>0% | 2<br>100.0% |

While the principles of this invention have been described in connection with specific embodiments, it should be understood clearly that these descriptions are made only by way of example and are not intended to limit the scope of the invention, in any manner. For example, a constituent panel comprising a combination of less than ten constituents is contemplated, so long as accuracy, sensitivity, and false positive parameters are not unduly compromised. Likewise, other variables or factors, e.g. hormonal levels or patterns as a gender subfactor, can be used to enhance accuracy through use of the multi-variate statistical techniques described herein. In such a manner, incorporation of additional factors in conjunction with a reduced panel can also provide useful means for identification. Other advantages and features of the invention will become apparent from the claims hereinafter, with the scope of the claims determined by the reasonable equivalents as understood by those skilled in the art.

TABLE 3c

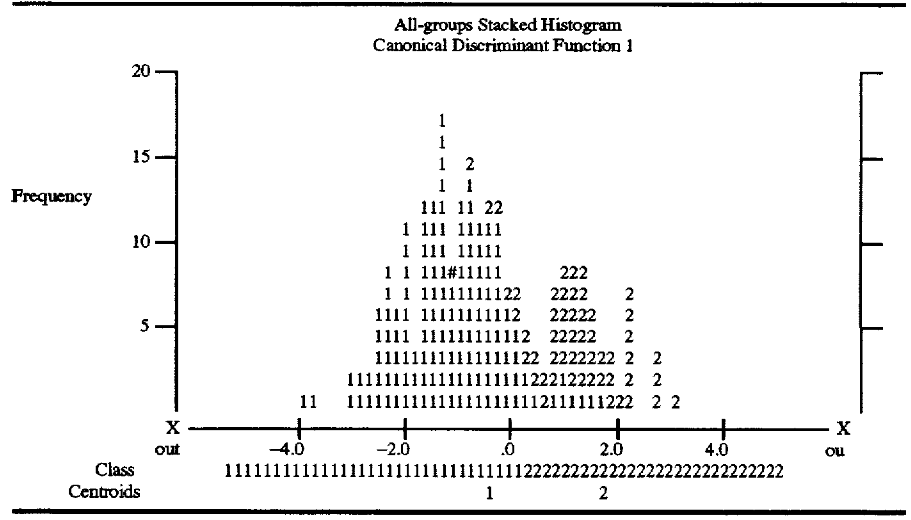

TABLE 3d

Classification results for cases selected for use in the analysis -

| Actual Group | | No. of Cases | Predicted Group Membership 1 | Predicted Group Membership 2 |
|---|---|---|---|---|
| Group | 1 | 134 | 117<br>87.3% | 17<br>12.7% |
| Group | 2 | 61 | 2<br>3.3% | 59<br>96.7% |
| Ungrouped cases | | 1 | 1<br>100.0% | 0<br>.0% |

Percent of "grouped" cases correctly classified: 90.26%

Classification results for cases selected for use in the analysis

What is claimed is:

1. A method of initially assessing alcohol consumption rates, comprising:

using a blood specimen from a human subject to develop an individual blood constituent panel, said panel having at least ten constituents including a ratio of direct bilirubin concentration to total bilirubin concentration as a constituent;

comparing said individual panel with a reference blood constituent panel to provide categories corresponding to rates of alcohol consumption, said blood reference panel including the ratio of direct bilirubin concentration to total bilirubin concentration as a constituent; and identifying the category of consumption rate for said subject indicated by said comparison.

2. The method as defined in claim 1 wherein said reference blood constituent panel includes value ranges for the level of each said constituent, whereby the relationship of one constituent to another can be determined.

3. The method as defined in claim 1 wherein said reference panel is developed using a pool of human subjects and prior probability values corresponding to the likelihood that said subject would be classified in a particular category of alcohol consumption.

4. The method as defined in claim 3 wherein there are a plurality of alcohol consumption categories, said categories corresponding to increasing alcohol consumption rates.

5. The method as defined in claim 4 wherein there are three categories of alcohol consumption.

6. The method as defined in claim 5 wherein:

a probability value of about 0.7–0.9 represents the lowest consumption rate;

a probability value of about 0.08–0.20 represents the intermediate consumption rate; and a probability value of about 0.01–0.10 represents the highest consumption rate.

7. The method as defined in claim 6 wherein the highest consumption rate is associated with the ratio of direct bilirubin concentration to total bilirubin concentration, said ratio a constituent of said individual and reference blood constituent panels.

8. The method as defined in claim 4 wherein said categories are derived from alcohol assessment standard instruments.

9. The method as defined in claim 8 wherein said instruments are selected from the group of psychological tests consisting of the Khavari Alcohol Test, the McAndrew Scale, and MODCRIT.

10. The method as defined in claim 8 wherein said instruments are volume frequency alcoholism assessment tests.

11. The method as defined in claim 10 wherein said instruments are selected from the group of psychological tests consisting of the Khavari Alcohol Test, the McAndrew Scale, and MODCRIT.

12. The method as defined in claim 1 wherein said comparison further includes use of a statistical analysis modifiable to preferentially identity one category of consumption rate over another.

13. The method as defined in claim 12 wherein said analysis is a multi-variate statistical technique.

14. The method as defined in claim 13 wherein said individual constituent panel is standardized.

15. The method as defined in claim 13 wherein said technique is selected from the group consisting of logistic regression, discriminant analysis, cluster analysis, factor analysis, and neuronetworking.

16. The method as defined in claim 12 wherein said statistical analysis incorporates factors selected from the group consisting of age, gender, race, nationality, diet, geography, socioeconomic status and drug interaction to increase the accuracy of said identification.

17. The method as defined in claim 1 further including a second comparison of said individual panel with said reference panel having an additional constituent such that said identification is made without false positive results.

18. The method as defined in claim 17 wherein said additional constituents are selected from the group consisting of selenium, β-hexacosanamine, carbohydrate deficient transferrin, and hemoglobin associated acetaldehyde.

19. A method of identifying individuals having a high alcohol consumption rate , said method comprising:

using a blood specimen from said subject to develop a subject blood constituent panel, said panel having at least ten constituents including a ratio of direct bilirubin concentration to total bilirubin concentration as a constituent;

comparing said subject panel with a first reference blood constituent panel, said reference panel including the ratio of direct bilirubin concentration to total bilirubin concentration as a constituent;

identifying the category of consumption rate for said subject indicated by said comparison; and minimizing false positive results with a second reference blood constituent panel as a reflex test off said first reference panel, said second reference panel including an additional constituent, said additional constituent being a blood alcohol marker.

20. The method as defined in claim 19 wherein said reference blood constituent panel includes value ranges corresponding to the level of each said constituent, whereby the relationship of one constituent to another can be determined.

21. The method as defined in claim 20 wherein said subject panel constituent values are converted to standard scores.

22. The method as defined in claim 20 wherein said reference panel is developed using a pool of human subjects and prior probability values corresponding to the likelihood that said subject would be classified in a particular category of alcohol consumption.

23. The method as defined in claim 22 wherein there are a plurality of alcohol consumption categories, said categories corresponding to increasing alcohol consumption rates.

24. The method as defined in claim 23 wherein there are three categories of alcohol consumption, said categories corresponding to increasing consumption rates of alcohol per unit time, and where such prior probability values are:

about 0.70–0.90 for that category reflecting the lowest consumption rate;

about 0.08–0.20 for that category reflecting the intermediate consumption rate; and about 0.01–0.10 for that category reflecting the highest consumption rate.

25. The method as defined in claim 22 wherein said categories are derived from alcohol assessment standard instruments.

26. The method as defined in claim 25 wherein said instruments are volume frequency alcoholism assessment tests.

27. The method as defined in claim 26 wherein said instruments are selected from the group consisting of the Khavari Alcohol Test, the McAndrew Scale, and MODCRIT.

28. The method as defined in claim 19 wherein said comparison further includes use of a statistical analysis modifiable to preferentially identify one category of consumption rate over another.

29. The method as defined in claim 28 wherein said analysis is a multi-variate statistical technique.

30. The method as defined in claim 29 wherein said technique is selected from the group consisting of logistic regression, discriminant analysis, cluster analysis, factor analysis, and neuron networking.

31. The method as defined in claim 28 wherein said statistical analysis incorporates factors selected from the group consisting of age, gender, race, nationality, diet, geography, socioeconomic status and drug interaction to increase the accuracy of said identification.

* * * * *

UNITED STATES PATENT AND TRADEMARK OFFICE

CERTIFICATE OF CORRECTION

PATENT NO. : 5,798,267

DATED : August 25, 1998

INVENTOR(S) : James W. Harasymiw

It is certified that error appears in the above-identified patent and that said Letters Patent is hereby corrected as shown below:

Col. 10, Line 58: Omit "transfenin" and insert -- transferrin --

Col. 16, Line 22: Omit "is" and insert -- in --

Col. 16, Line 23: Omit "p>0.0001" and insert -- p<0.0001 --

On the title page, item [56]:

Col. 2, Line 12: Omit "Alcohol Alcohol. 1985" and insert -- Alcohol & Alcoholism, 1986 --

Signed and Sealed this

Twenty-seventh Day of March, 2001

Attest:

NICHOLAS P. GODICI

Attesting Officer

*Acting Director of the United States Patent and Trademark Office*